(12) United States Patent
Enomoto et al.

(10) Patent No.: US 9,808,407 B2
(45) Date of Patent: Nov. 7, 2017

(54) POROUS SILICA PARTICLE, METHOD FOR PRODUCING THE SAME, AND COSMETIC CONTAINING THE SAME

(71) Applicant: JGC Catalysts and Chemicals Ltd., Kawasaki-Shi, Kanagawa (JP)

(72) Inventors: Naoyuki Enomoto, Kitakyushu (JP); Satoshi Watanabe, Kitakyushu (JP); Yasutaka Miyoshi, Kitakyushu (JP)

(73) Assignee: JGC CATALYSTS AND CHEMICALS LTD., Kawasaki-Shi, Kanagawa (JP)

( * ) Notice: Subject to any disclaimer, the term of this patent is extended or adjusted under 35 U.S.C. 154(b) by 0 days.

(21) Appl. No.: 15/318,431

(22) PCT Filed: Jun. 30, 2015

(86) PCT No.: PCT/JP2015/068872
§ 371 (c)(1),
(2) Date: Dec. 13, 2016

(87) PCT Pub. No.: WO2016/002797
PCT Pub. Date: Jan. 7, 2016

(65) Prior Publication Data
US 2017/0135920 A1    May 18, 2017

(30) Foreign Application Priority Data

Jun. 30, 2014  (JP) .................. 2014-134192

(51) Int. Cl.
| A61K 8/25 | (2006.01) |
| A61K 8/29 | (2006.01) |
| A61K 8/19 | (2006.01) |
| A61Q 1/12 | (2006.01) |
| A61K 8/02 | (2006.01) |
| A61Q 1/02 | (2006.01) |

(52) U.S. Cl.
CPC .............. *A61K 8/25* (2013.01); *A61K 8/0279* (2013.01); *A61K 8/19* (2013.01); *A61K 8/29* (2013.01); *A61Q 1/02* (2013.01); *A61Q 1/12* (2013.01); *A61K 2800/412* (2013.01)

(58) Field of Classification Search
None
See application file for complete search history.

(56) References Cited

U.S. PATENT DOCUMENTS

| 4,132,560 A | 1/1979 | Marquisee et al. |
| 5,911,963 A | 6/1999 | Krivak et al. |
| 2006/0034788 A1 | 2/2006 | Horino et al. |
| 2010/0247914 A1* | 9/2010 | Enomoto ................. A61K 8/25 428/402 |
| 2013/0004772 A1* | 1/2013 | Lofton ..................... B01J 20/08 428/402.24 |
| 2015/0251150 A1 | 9/2015 | Enomoto et al. |

FOREIGN PATENT DOCUMENTS

| EP | 1493433 A1 | 1/2005 |
| FR | 2105908 A5 | 4/1972 |
| JP | S61174103 A | 8/1986 |
| JP | 2002160907 A | 6/2002 |
| JP | 2005298739 A | 10/2005 |
| JP | 2007238426 A | 9/2007 |
| JP | 2008120633 A | 5/2008 |
| JP | 2009137806 A | 6/2009 |
| JP | 2010138021 A | 6/2010 |
| JP | 2010138022 A | 6/2010 |
| JP | 2010155750 A | 7/2010 |
| JP | 2013095888 A | 5/2013 |
| JP | 2013136493 A | 7/2013 |

OTHER PUBLICATIONS

International Search Report dated Sep. 1, 2015 issued in corresponding International Application No. PCT/JP2015/068872.
Japanese Decision to Grant a Patent dated Apr. 19, 2016 issued in corresponding Japanese Patent Application No. 2016-508899.
Office Action dated Jan. 12, 2017 for the correspoinding Korean Patent Appllication No. 10-2016-7035283.
Extended European Search Report dated Mar. 20, 2017 for the corresponding European Patent Application No. 15816068.9.

* cited by examiner

*Primary Examiner* — Robert A Wax
*Assistant Examiner* — Quanglong N Truong
(74) *Attorney, Agent, or Firm* — Troutman Sanders LLP

(57) ABSTRACT

An object of the present invention is to provide a porous silica particle with the small specific surface area and the large pore volume, a method for producing the same, and a cosmetic containing the porous silica particle with such characteristics as the texture improver. The porous silica particle according to the present invention has a structure sparsely packed with silica microparticles. The mean particle diameter is 0.5 to 25 µm, the specific surface area measured by the BET method is 5 to 60 $m^2/cm^3$, and the pore volume is 0.35 to 2.0 ml/g. In the pore size distribution of the porous silica particles (X axis: pore diameter, Y axis: value obtained by differentiating the pore volume by the pore diameter), the most frequent pore diameter ($D_m$) satisfies $100 < D_m < 4000$ [nm].

8 Claims, 2 Drawing Sheets

POROUS SILICA PARTICLE, METHOD FOR PRODUCING THE SAME, AND COSMETIC CONTAINING THE SAME

CROSS-REFERENCE TO RELATED APPLICATIONS

This is a U.S. national phase application under 35 U.S.C. §371 of International Patent Application No. PCT/JP2015/068872, filed Jun. 30, 2015, and claims benefit of priority to Japanese Patent Application No. 2014-134192, filed Jun. 30, 2014. The entire contents of these applications are hereby incorporated by reference.

TECHNICAL FIELD

The present invention relates to a porous silica particle with the small specific surface area and the large pore volume, a method for producing the same, and a cosmetic containing the same.

BACKGROUND

There are various known methods for producing porous silica particles. For example, Japanese Unexamined Patent Application Publication No. S61-174103 discloses the method in which the colloidal solution containing primary particles (silica microparticles) with a mean particle diameter of 2500 Å or less is sprayed and dried using a spray drier, so that porous silica particles with a mean particle diameter of 1 to 20 μm are prepared.

Japanese Unexamined Patent Application Publication No. 2002-160907 discloses the method in which the colloidal solution is sprayed and dried to provide inorganic silica microparticle aggregates with a mean particle diameter of 1 to 100 μm including inorganic silica microparticles with a mean particle diameter of 2 to 250 nm. Then, this aggregate is coated with an oxide layer, so that spherical porous particles are made.

In addition, Japanese Unexamined Patent Application Publication No. 2010-138021 discloses making of the porous silica particles with a mean particle diameter of 0.5 to 50 μm and a specific surface area of 30 to 250 $m^2/g$ by spraying and drying the dispersion liquid containing silica microparticles of 10 to 50 nm. Japanese Unexamined Patent Application Publication No. 2010-138022 discloses making of the porous silica particles with a mean particle diameter of 0.5 to 50 μm and a specific surface area of 10 to 100 $m^2/g$ by spraying and drying the dispersion liquid containing silica microparticles of 50 to 300 nm. Japanese Unexamined Patent Application Publication No. 2005-298739 discloses making of the porous silica particles by spraying and drying the slurry containing the ceramic powder and the material which disappears due to the chemical reaction or the change in state occurring at a temperature of 40° C. to 250° C.

It has been generally known that cosmetics contain spherical porous silica particles and the like as the texture improver. For example, Japanese Unexamined Patent Application Publication No. 2009-137806 discloses the method of obtaining the powder solid cosmetic containing the porous silica particles to have the texture characteristics such as the smoothness, the moistness, the rolling effect, the even spreadability, the adhesive property, and the continuing rolling effect. These texture characteristics are typically required for the texture improver of the cosmetic.

However, it is concerned that the aforementioned porous silica particles might be categorized as the nanomaterial described below. In the announcement made by the European Commission as of Oct. 18, 2011, (1) the substances or materials containing particles for more than 50% in the number size distribution in the range of 1 to 100 nm, and (2) the substances or materials with a specific surface area (SA) per unit volume of more than 60 $m^2/cm^3$ are categorized as the nanomaterial. The aforementioned porous silica particles have both the nanometer-size pores and the large specific surface area. The specific surface area per unit weight converted at a silica density of 2.2 $g/cm^3$ is more than 27 $m^2/g$. It has not been verified that the particles categorized as the nanomaterial directly lead to the serious problem in environment, health, or safety but users and consumers will demand to avoid using the particles categorized as the nanomaterial.

If the definition of the nanomaterial is introduced to REACH in the future, it may be possible that the particles categorized as the nanomaterial cannot be used freely in the industrial use. It may be also possible that the submission of various kinds of documents for the use of the particles categorized as the nanomaterial is required. Therefore, the time and cost may be required in the procedure.

SUMMARY

In view of the above, it is an object of the present invention to provide a porous silica particle with the small specific surface area and the large pore volume. Such a porous silica particle has the excellent texture characteristics. In addition, the definition of the nanomaterial does not apply to this porous silica particle. Therefore, the porous silica particle according to the present invention can be used without anxiety in the purposes similar to the typical porous silica particles. Moreover, the present invention can provide a cosmetic containing the porous silica particle with such characteristics as the texture improver.

The porous silica particle according to the present invention contains silica microparticles. The mean particle diameter of the porous silica particles is 0.5 to 25 μm, the specific surface area thereof obtained by the BET method is 5 to 60 $m^2/cm^3$, and the pore volume thereof is 0.35 to 2.0 ml/g.

In the pore size distribution of the porous silica particles (X axis: pore diameter, Y axis: the value obtained by differentiating the pore volume by the pore diameter), the most frequent pore diameter ($D_m$) is more than 100 nm and less than 4000 nm.

In addition, the porous silica particles are prepared so that, in the pore size distribution of the porous silica particles, the minimum pore diameter ($D_0$) is in the range of 25 to 500 nm, the maximum pore diameter ($D_{100}$) is in the range of 300 to 8000 nm, and the ratio of the maximum pore diameter ($D_{100}$) to the minimum pore diameter ($D_0$), ($D_{100}/D_0$), is in the range of 4 to 320.

The porous silica particles may contain, in the range of 10 to 50 wt %, inorganic oxide microparticles containing at least one of titanium dioxide, iron oxide, and zinc oxide. The porous silica particles may alternatively contain organic microparticles.

The mean particle diameter of the silica microparticles is preferably in the range of 0.01 to 0.30 times the mean particle diameter of the porous silica particles.

A manufacturing method for the porous silica particle according to the present invention includes: (A) a step of dispersing silicate binder with a solid content concentration of 1 to 40 wt % to silica sol with a mean particle diameter of more than 100 nm and 1000 nm or less and a solid content concentration of 10 to 30 wt %, thereby obtaining slurry; and (B) a step of spraying a spray liquid including the slurry into an air flow, thereby obtaining porous silica particles.

The cosmetic according to the present invention contains any of the aforementioned porous silica particles.

The porous silica particle according to the present invention has the large pore volume though the specific surface area thereof is small. Therefore, the definition of the nanomaterial does not apply to the porous silica particle according to the present invention. Thus, the porous silica particle according to the present invention can be used without anxiety in the purposes similar to the typical porous silica particles. In particular, the porous silica particle according to the present invention has the less raspy feeling when mixed into the cosmetic, in which point the porous silica particle according to the present invention is different from the typical porous silica particles. Therefore, the porous silica particle according to the present invention can provide the cosmetic with the texture characteristics including the high sliding texture.

DETAILED DESCRIPTION

<Silica Microparticle>

Figure 1:
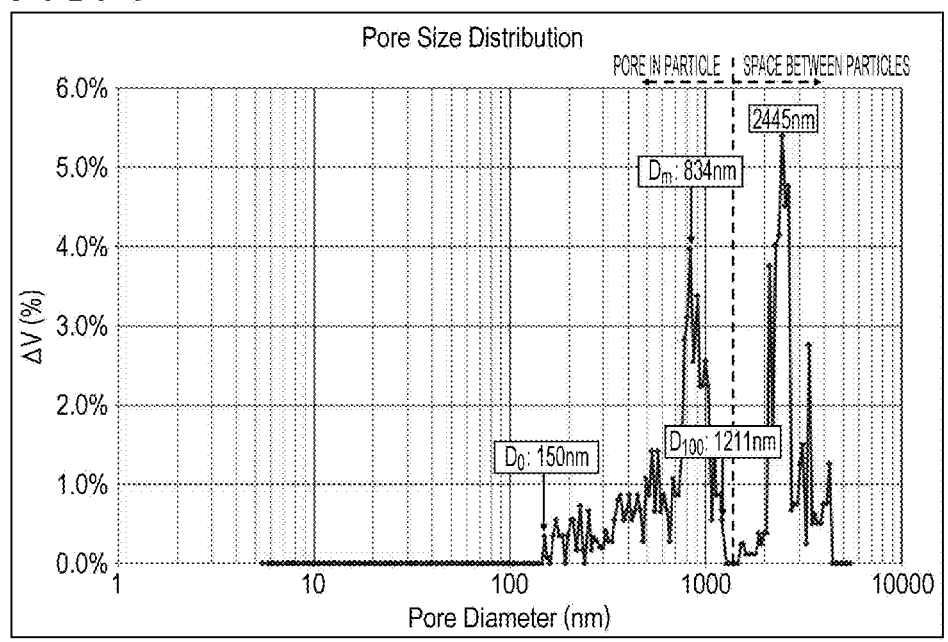
FIG. 1 is a graph of the pore size distribution (X axis: pore diameter, Y axis: value obtained by differentiating the pore volume by the pore diameter) of porous silica particles according to Example 1.

Examples of the silica microparticles contained in the porous silica particle used in the present invention include silica-alumina, silica-zirconia, and silica-titania, other than silica. It is not necessary to change the production conditions for the porous silica particle depending on the composition of the silica microparticle. In consideration of mixing into the cosmetic, the silica microparticle is preferably amorphous silica.

The sphericity of the silica microparticle is preferably 0.85 to 1.00. The sphericity here is obtained as follows: in the photograph projection diagram obtained by photographing with the transmission electron microscope, arbitrary 50 particles are selected and the maximum diameter (DL) of each particle and the short diameter (DS) orthogonal to the maximum diameter (DL) are obtained, and the mean value of the ratio (DS/DL) corresponds to the sphericity. A sphericity of less than 0.85 is not preferable because such sphericity will largely influence the strength of the porous silica particle.

The mean particle diameter ($d_2$) of the silica microparticles is preferably more than 100 nm and 1000 nm or less. The coefficient of variation of the particle diameter (CV value) is preferably 5 to 15%. Thus, the definition of the nanomaterial does not apply to the porous silica particle obtained by the silica microparticles with the mean particle diameter in this range. Therefore, the porous silica particle according to the present invention can be used without anxiety in the purposes similar to the typical porous silica particles. The mean particle diameter ($d_2$) is desirably in the range of 110 to 600 nm, particularly preferably 120 to 550 nm.

When the silica microparticles with a sphericity of 0.85 to 1.00 are used and the coefficient of variation of the particle diameter (CV value) is more than 15%, the strength of the porous silica particles will be largely influenced. Such silica microparticles are therefore not preferable. It is more desirable that the coefficient of variation of the particle diameter of the silica microparticle (CV value) is less than 5% in the present invention. However, it is not easy to industrially produce the silica microparticles with such a particle size distribution.

<Porous Silica Particle>

The porous silica particle according to the present invention contains the silica microparticles. The mean particle diameter ($d_1$) of the porous silica particles according to the present invention is 0.5 to 25 μm, the specific surface area thereof obtained by the BET method is 5 to 60 m$^2$/cm$^3$, and the pore volume thereof is 0.35 to 2.0 ml/g. The mean particle diameter can be obtained by the laser diffraction method. If the porous silica particles with a mean particle diameter of less than 0.5 μm are used, the user who touches the particle powder does not feel the rolling effect as the spherical powder and also feels the poor spreadability. On the other hand, if the porous silica particles with a mean particle diameter of more than 25 μm are used, the user feels the raspy feeling from the particle powder. The mean particle diameter ($d_1$) of the porous silica particles is preferably in the range of 2 to 10 μm.

If the specific surface area per unit volume obtained by the BET method is less than 5 m$^2$/cm$^3$, more particles have the shapes other than the spherical or near-spherical shape. Therefore, the typical texture characteristics required for the texture improver of the cosmetic (such as the smoothness, the moistness, the rolling effect, the even spreadability, the adhesive property, and the continuing rolling effect) drastically deteriorate. The porous silica particles whose specific surface area per unit volume obtained by the BET method is more than 60 m$^2$/cm$^3$ (in the case of silica, 27 m$^2$/g) are categorized as the nanomaterial.

In addition, the porous silica particle having a pore volume of less than 0.35 ml/g has the low porosity. Such a particle absorbs less oil in the pores. Moreover, since such a particle becomes heavier in this case, the user who touches the particle powder will feel less smoothness, rolling effect, even spreadability, and continuing rolling effect. On the other hand, the porous silica particle having a pore volume of more than 2.0 ml/g has the high porosity and the low particle strength. In this case, the particles will easily collapse when applied on the skin. As a result, the continuing rolling effect will drastically decrease.

In the pore size distribution of the porous silica particles (X axis: pore diameter, Y axis: the value obtained by differentiating the pore volume by the pore diameter), the most frequent pore diameter ($D_m$) is in the range of more than 100 nm and less than 4000 nm ($100 < D_m < 4000$ [nm]). If the most frequent pore diameter ($D_m$) is 100 nm or less, it is practically difficult to achieve both the desired pore volume "0.35 ml/g or more" and the desired specific surface area "60 m$^2$/cm$^3$ or less" (in the case of silica, 27 m$^2$/g or less). The most frequent pore diameter (Dm) of 4000 nm or more is not preferable because such diameter will lower the strength of the particle easily. The most frequent pore diameter ($D_m$) is preferably in the range of more than 150 and less than 3000 nm ($150<D_m<3000$), and more preferably in the range of more than 200 and less than 2000 nm ($200<D_m<2000$).

Description is made of the pore size distribution with reference to FIG. 1. FIG. 1 shows the pore size distribution of the porous silica particles made in Example 1 to be described below. In FIG. 1, X axis represents the pore diameter and Y axis represents the value ($\Delta V$) obtained by differentiating the pore volume by the pore diameter. Between two distribution curves, a certain pore diameter value (expressed with a dashed line in the graph) on X axis is present. Namely, FIG. 1 shows that the pore diameter with $\Delta V$ of 0% exists between a first distribution curve that depends on the pores existing in the porous silica particles and a second distribution curve that depends on the space between the porous silica particles.

In the first distribution curve, the smallest pore diameter $D_0$ among the diameters at which the $\Delta V$ is measured corresponds to the minimum pore diameter. The pore diameter $D_m$ at a first peak (the maximum value of $\Delta V$ in the first distribution curve) is the most frequent pore diameter. The pore diameter $D_{100}$ at the right end (the maximum diameter among the diameters at which the $\Delta V$ is measured) corresponds to the maximum pore diameter.

Note that in FIG. 1, the most frequent pore diameter ($D_m$) is 834 nm, the minimum pore diameter ($D_0$) is 150 nm, and the maximum pore diameter ($D_{100}$) is 1211 nm. The second distribution curve has a peak at 2445 nm.

The porous silica particle has a structure sparsely packed with the silica microparticles (primary particles formed by silica sol). Therefore, in the pore size distribution of the porous silica particles, the minimum pore diameter ($D_0$) is in the range of 25 to 500 nm, the maximum pore diameter ($D_{100}$) is in the range of 300 to 8000 nm, and the ratio of the maximum pore diameter ($D_{100}$) to the minimum pore diameter ($D_0$), ($D_{100}/D_0$), is in the range of 4 to 320.

If the minimum pore diameter ($D_0$) is less than 25 nm, it is practically difficult to achieve both the desired pore volume (0.35 ml/g or more) and the desired specific surface area (60 $m^2/cm^3$ or less). The minimum pore diameter ($D_0$) of more than 500 nm is not preferable because such diameter will lower the strength of the particle easily. Moreover, if the maximum pore diameter ($D_{100}$) is less than 300 nm, it is practically difficult to achieve both the desired pore volume and the desired specific surface area. The maximum pore diameter ($D_{100}$) of more than 8000 nm is not preferable because such diameter will lower the strength of the particle easily. Moreover, if the ratio of the maximum pore diameter ($D_{100}$) to the minimum pore diameter ($D_0$), $D_{100}/D_0$, is less than 4 or more than 320, it is also practically difficult to achieve both the desired pore volume and the desired specific surface area.

The minimum pore diameter ($D_0$) is particularly desirably 50 to 400 nm. The maximum pore diameter ($D_{100}$) is particularly desirably 500 to 4000 nm. The pore diameter ratio ($D_{100}/D_0$) is preferably in the range of 4 to 80, particularly desirably in the range of 4 to 20.

The porous silica particle includes such pores. The total volume of the pores with a pore diameter in the range of ($D_m$ (the most frequent pore diameter)$\times 0.75$ to $D_m \times 1.25$) nm constitutes less than 70% of the total pore volume. Patent Literature 4 discloses porous silica particle with the structure in which silica microparticles are densely packed. In this case, it has been known that the total volume of the pores constitutes 70% or more of the total pore volume.

Figure 2:
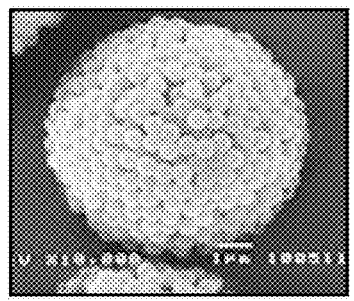
FIG. 2 is a SEM photograph (magnification: 10,000) obtained by photographing the external appearance of the porous silica particle according to Example 1 with the scanning electron microscope.
Figure 3:
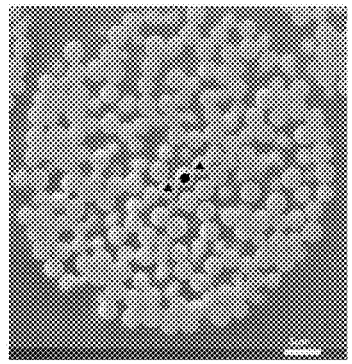
FIG. 3 is a SEM photograph (magnification: 10,000) obtained by photographing the cross section of the porous silica particle according to Example 1 with the scanning electron microscope.
Figure 4:
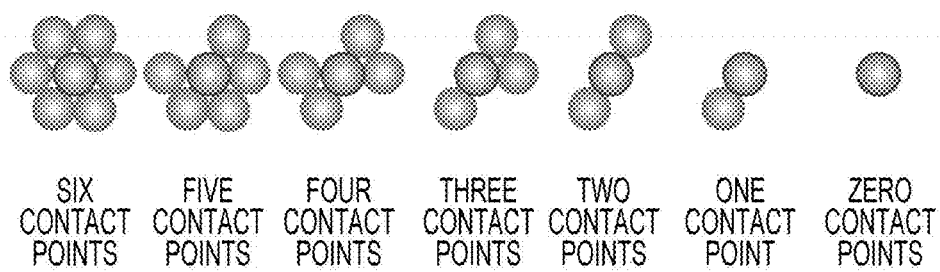
FIG. 4 is a model diagram for describing the number of contact points.

In this manner, the porous silica particle according to the present invention has the sparsely packed structure. This structure will be described using the photograph (SEM photograph) obtained with the electron microscope. FIG. 2 is the SEM photograph (magnification: 10,000) of the porous silica particle made in Example 1 to be described below. A plurality of silica microparticles is joined together while leaving a number of gaps so that the sparsely packed structure is formed. Accordingly, the uneven structure on the surface of the porous silica particle is formed. FIG. 3 is the SEM photograph (magnification: 10,000) obtained by putting the porous silica particles in the liquid resin, curing the liquid resin, and then photographing the cross section of this particle. With this photograph, the number of contact points between the central microparticle (silica microparticle) of the spherical porous silica particle and other adjacent microparticles is measured. Based on this, the sparsely packed structure can be confirmed. FIG. 4 is a model diagram for describing the number of contact points between one particle in the center of the porous silica particle and the adjacent particle or particles. Six contact points indicate the densely packed structure, which corresponds to the most densely filled structure. However, the number of contact points may exceed six if the particle size distribution of the silica microparticles is wide and the silica microparticles contain a number of smaller particles or larger particles than the mean particle diameter. In the present invention, the porous silica particles have the sparsely packed structure with four or less contact points. As the number of contact points is smaller, the pore volume is larger even if the specific surface area is the same. The number of contact points is preferably three or less, more preferably two or less. If the number of contact points is more than four, i.e., if the porous silica particle has the densely packed structure (for example, six contact points), the particles with the large pore volume cannot be obtained. The measured number of contact points of the porous silica particle in FIG. 3 is two. In FIG. 3, the number of contact points is larger near the surface of the particle than in the center. Therefore, the microparticles with the six contact points may be observed in a part. In this manner, the porous silica particle has the structure in which the number of contact points of the silica microparticle is larger on the surface (outer circumference) than in the center. This is the reason why the range of the ratio of the maximum pore diameter ($D_{100}$) to the minimum pore diameter ($D_0$), ($D_{100}/D_0$), becomes larger ($4 \leq (D_{100}/D_0) \leq 320$). In addition, it is considered that this structure will cause the porous silica particle to have a compression strength of 10 MPa or more as described below.

The mean particle diameter ($d_2$) of the silica microparticles is in the range of 0.01 to 0.30 times, preferably 0.02 to 0.20 times, the mean particle diameter ($d_1$) of the porous silica particles. Within this range, the particle surface has the optimum unevenness and the skin contact area can be controlled, so that the rolling resistance is reduced. Thus, when the particle powder is touched or is mixed in the cosmetic, the raspy feeling is not felt and the texture characteristics including the high sliding texture can be achieved.

The compression strength of the porous silica particle is desirably 10 MPa or more, particularly desirably 30 MPa or more. If the compression strength is less than 10 MPa, the particles may collapse in the process of mixing the particles in the cosmetic. In this case, the desired texture characteristics may not be obtained. The upper limit of the compression strength is not particularly limited. The upper limit of the compression strength may be, for example, approximately 200 MPa.

In addition, the porous silica particle may include 50 wt % or less of inorganic oxide microparticles containing at least one of titanium dioxide, iron oxide, and zinc oxide. Within this range, the porous silica particle can contain the inorganic oxide microparticles uniformly inside the particle. The iron oxide is preferably ferric oxide, iron hydroxide oxide, or triiron tetraoxide. The mean particle diameter of the inorganic oxide microparticles is desirably at the same level as that of the silica microparticles. Therefore, the mean particle diameter of the inorganic oxide microparticles is suitably in the range of 100 to 1000 nm.

The porous silica particle may alternatively contain organic microparticles. The organic microparticles will be described below. The porous silica particle may contain binder. The binder is silica-based binder.

<Method for Producing Porous Silica Particle>

A method for producing the porous silica particle according to the present invention includes the following steps (A) and (B).

(A) A slurry preparation step of dispersing silicate binder with a solid content concentration in the range of 1 to 40 wt % to silica sol with a mean particle diameter of more than 100 nm and 1000 nm or less and a solid content concentration of 10 to 30 wt %, thereby preparing dispersion slurry.

(B) A spray drying step of spraying a spray liquid containing the dispersion slurry in the air flow, thereby preparing the porous silica particle.

Description will be made of each step.

<Step (A)>

The concentration of the silica sol is in the range of 10 to 30 wt % in solid content conversion. The concentration of the silicate binder is in the range of 1 to 40 wt % in solid content conversion. When the silica sol and the silicate binder are used in this range, the binder component in the particle turns into the gel in the initial stage of the drying in the step of spraying and drying. Thus, the structure (condensed structure) sparsely packed with the constituent primary particles (silica microparticles) including silica sol is formed. As a result, the porous silica particles with the large pore volume despite of having the small specific surface area can be prepared. The silicate binder has an effect of attaching together the constituent primary particles (silica microparticles) containing the silica sol. Thus, the porous silica particles with the high mechanical strength can be prepared.

The solid content concentration (in carbon dioxide conversion) of the silicate binder in the slurry is preferably 1.5 to 10.0 wt %. The particularly preferable range is 2.0 to 5.0 wt %. If the solid content concentration is less than 1.5 wt %, the structure densely packed with the silica microparticles is easily formed. This makes it difficult to prepare the porous silica particle with the large pore volume. Over 10.0 wt %, the stability of the silicate binder is decreased. Therefore, the microscopic gel-like silica or the particulate silica is generated over time and the specific surface area is increased. As a result, the solid content concentration of the silicate binder is not preferably over 10.0 wt %.

<Step (B)>

The spraying and drying may be carried out based on the known method using a commercial spray drier (for example, the disk rotating type or the nozzle type). For example, the spray liquid may be sprayed into a hot air flow at a speed of 1 to 3 liters per minute. In the spraying, the entrance temperature of the hot air is preferably in the range of 70 to 400° C. and the exit temperature thereof is preferably in the range of 40 to 60° C. If the entrance temperature is less than 70° C., the solid part of the dispersion liquid is not dried sufficiently; if the entrance temperature is more than 400° C., the shape of the particle becomes distorted in the spraying and drying. If the exit temperature is less than 40° C., the solid part is not dried sufficiently and the undried component may adhere to the inside of the apparatus. The entrance temperature is more preferably in the range of 100 to 300° C.

By the spraying and drying, a dried powder of the porous silica particles is formed. By calcining this dried powder, a powder mainly containing the calcined porous silica particles (hereinafter referred to as the porous silica particles simply) is obtained. Namely, by calcining the dried powder at 200 to 800° C. for 1 to 24 hours, the powder of the porous silica particles can be produced. The calcination increases the compression strength of the powder. If the calcination temperature is less than 200° C., the siloxane bond between the primary particles contained in the porous silica particle is not sufficient, so that the improved compression strength is not expected. On the other hand, if the calcination temperature is more than 800° C., the pores in the particle disappear due to the sintering of the particles, so that the desired porosity cannot be maintained. In addition, the crystalline silica (such as quartz) may be generated. If the calcination time is less than 1 hour, the siloxane bond between the primary particles is not sufficient, so that the improved compression strength is not expected. If the calcination time is more than 24 hours, the particular effect cannot be obtained and this is not economical.

In addition, the silicate binder may be formed by dealkalizing (for example, removing Na ions from) a silicate aqueous solution of alkali metal silicate or a silicate of an organic base with the cation exchange resin. Examples of the silicate include the silicate of the organic base, for example, the quaternary ammonium silicate and an alkali metal silicate such as sodium silicate (water glass) or potassium silicate.

The spray liquid may contain inorganic oxide microparticles as the metal oxide other than the aforementioned silica as necessary. The mean particle diameter of the inorganic oxide microparticles is desirably approximately the same as that of the silica microparticles. That is to say, the mean particle diameter of the inorganic oxide microparticles is 100 to 1000 nm. The inorganic oxide microparticles have the optical characteristics including the coverage of the skin and the UV light blocking when applied to the skin. The inorganic oxide microparticles applied on the skin provide the less raspy feeling and can therefore achieve the optical characteristics and the texture characteristics including the high sliding texture.

The spray liquid may contain the organic microparticles as necessary. Examples of the organic microparticles include particles of polymer latex such as natural rubber, a styrene-butadiene copolymer, acrylate latex, and polybutadiene. The mean particle diameter of the organic microparticles is preferably in the range of 25 to 1000 nm, particularly preferably in the range of 100 to 1000 nm.

By heating the porous silica particles containing the organic microparticles at 400 to 1200° C. under the atmospheric pressure or reduced pressure, the organic microparticles may be removed. This can prepare the porous silica particles with the larger pore volume.

<Cosmetic>

Detailed description will be made of cosmetics formed by mixing the porous silica particles and various cosmetic components but the present invention is not limited to the following cosmetics.

Examples of the various cosmetic components include: oils and fats such as olive oil, rapeseed oil, and beef tallow;

waxes such as jojoba oil, carnauba wax, candelilla wax, and beeswax; hydrocarbons such as paraffin, squalane, synthetic or vegetable squalane, α-olefin oligomer, microcrystalline wax, pentane, and hexane; fatty acids such as stearic acid, myristic acid, oleic acid, and α-hydroxy acid; alcohols such as isostearyl alcohol, octyldodecanol, lauryl alcohol, ethanol, isopropanol, butyl alcohol, myristyl alcohol, cetanol, stearyl alcohol, and behenyl alcohol; alkyl glyceryl ethers; esters such as myristic acid isopropyl, palmitic isopropyl, stearic acid ethyl, oleic acid ethyl, lauric acid cetyl, and oleic acid decyl; polyvalent alcohols such as ethylene glycol, triethylene glycol, polyethylene glycol, propylene glycol, glycerin, and diglycerin; saccharides such as sorbitol, glucose, sucrose, and trehalose; silicone oils such as methylpolysiloxane, methylhydrogenpolysiloxane, methylphenyl silicone oil, various modified silicone oils, and cyclicdimethyl silicon oils; silicone gel crosslinked with a silicone organic compound and/or another organic compound; various surfactants such as nonionic surfactants, cationic surfactants, anionic surfactants, amphoteric surfactants, and amphoteric surfactants; fluorine oils such as perfluoropolyether; gum arabic, carrageenan, agar, xanthan gum, gelatin, alginic acid, guar gum, albumin, pullulan, carboxyvinylpolymer, cellulose, and derivatives thereof; various polymers such as polyacrylic acid amide, polyacrylic acid sodium, and polyvinyl alcohol; various surfactants such as anionic surfactants, cationic surfactants, and nonionic surfactants; animal and plant extracts; amino acids; peptides; vitamins; UV-ray protector, bactericide, sterilizer, and antioxidant, for example, cinnamic acids such as octyl paramethoxycinnamate, salicylic, benzoate, urocanic, and benzophenoic substances; modified or unmodified clay minerals; solvents such as butyl acetate, acetone, and toluene; and titanium dioxide, zinc oxide, aluminum oxide, aluminum hydroxide, red oxide, yellow iron oxide, black iron oxide, cerium oxide, zirconium oxide, silica, mica, talc, sericite, boron nitride, barium sulfate, titanated mica with the pearl-like gloss, a composite thereof, various organic pigments, various organic dyes, water, and flavoring agents having various particle diameters, particle size distributions and shapes. The inorganic compound such as titanium dioxide or zinc oxide may be the inorganic compound with a surface having been subjected to the silicone process, the fluorine process, the metal soap process, or the like.

Moreover, the resin particles of polyacrylic acid methyl, nylon, silicone resin, silicone rubber, polyethylene, polyester, polyurethane, or the like may be contained.

Any of the following components with the whitening effect may be contained: arbutin, kojic acid, vitamin C, sodium ascorbate, ascorbic acid phosphate ester magnesium, di-palmitic acid ascorbyl, glucoside ascorbate, and other ascorbic acid derivatives; and a placental extract, sulfur, an oil-soluble licorice extract, a mulberry extract, and other plant extracts, linolic acid, linoleic acid, lactic acid, and tranexamic acid.

Any of the following components with the skin improving effect may be contained: the components with the anti-aging effect such as vitamin C, carotenoid, flavonoid, tannin, a caffeic derivative, lignan, saponin, retinoic acid, a retinoic acid structure analogue, N-acetylglucosamine, and α-hydroxy acid; polyvalent alcohols such as glycerin, propylene glycol, and 1,3-butylene glycol; saccharides such as high-fructose mixture, trehalose, and pullulan; biopolymers such as sodium hyaluronate, collagen, elastin, chitin and chitosan, and sodium chondroitin sulfate; amino acid, betaine, ceramide, sphingolipid, ceramide, cholesterol, and derivatives thereof; ϵ-aminocaproic acid; glycyrrhizic acid; and various vitamins.

In addition, the cosmetic components described in, for example, Japanese Standards of Quasi-drug Ingredients 2006 (issued by YAKUJI NIPPO LIMITED. on June 16, Heisei 18) and International Cosmetic Ingredient Dictionary and Handbook (issued by the Cosmetic, Toiletry, and Fragrance Association, Eleventh Edition 2006) can be used.

The cosmetic according to the present invention can be produced by a normal method that has been known. The cosmetic is used in various forms, for example, in the shape of powder, cake, pencil, stick, cream, gel, mousse, liquid, or cream. Specific examples of the cosmetic include: cosmetics for washing, such as the soap, the cleansing foam, and the make-up remover cream; skincare cosmetics for moisturizing, skin protection, treating acne and cuticle, massaging, treating wrinkle, sag, dullness, and dark rings under the eyes, blocking the UV ray, whitening, and antioxidation; base makeup cosmetics such as the powder foundation, the liquid foundation, the cream foundation, the mousse foundation, the pressed powder, and the base of the makeup; makeup cosmetics for the face other than the foundation, such as the eye shadow, the eyebrow powder, the eyeliner, the mascara, and the lipstick; cosmetics for the hair, such as the material for fostering the hair, preventing the dandruff, preventing itching, washing the hair, conditioning/styling the hair, perming or curling the hair, and coloring and bleaching the hair; cosmetics for the body, such as the material for washing the body, protecting the body from sunlight, preventing the hand from becoming rough, slimming the body, improving the blood flow, preventing itching, preventing the smell of body, antiperspirant, treating the hair, repelling insects, and the body powder; a flagrance cosmetic such as perfume, eau de parfum, eau de toilette, eau de cologne, shower cologne, solid perfume, body lotion, and bath oil; oral health care products such as tooth brushing and mouth washing products.

EXAMPLES

Specific examples of the present invention will be described below but the examples will not limit the present invention.

Example 1

Silica sol with a silica concentration of 40 wt % for 2000 g is prepared by condensing 4000 g of silica sol (manufactured by JGC Catalysts and Chemicals Ltd.: SS-550 with a mean particle diameter of 550 nm and a silica concentration of 20 wt %) with the use of an ultrafiltration membrane (SIP-1013, manufactured by Asahi Kasei Corporation). The obtained silica sol is subjected to cation exchange to adjust the pH to be 2.0, thereby providing silica sol (I). Here, the variation of coefficient (CV value) and the sphericity of the silica microparticles are measured by a method to be described below. Table 1 shows the characteristics of the silica sol (I) used in the examples.

On the other hand, after water glass (JIS-3) is diluted with pure water, the mixture is subjected to the cation exchange, so that a silicate solution (with a silica sol concentration of 10.0 wt %) is prepared. Then, 889 g of the silicate solution is added to 2000 g of the silica sol (I), so that dispersion slurry with a silica sol concentration of 27.7 wt %, a concentration of 3.1 wt % of silicate derived from the water glass, and a solid content concentration of 30.8 wt % is obtained.

The obtained slurry is used as the spray liquid. The spray liquid is sprayed and dried using the spray drier (NIRO-ATMIZER, manufactured by NIRO). Specifically, the slurry is supplied at a flow rate of 2 L/hr through one of two fluid nozzles and gas is supplied through the other nozzle at a pressure of 0.4 MPa into the dry air flow with an entrance temperature set to 220° C. and an exit temperature set to 50 to 55° C., and thus the slurry is sprayed and dried. In this manner, the dried powder containing the porous silica particles is obtained. The conditions of preparing the dried powder are shown in Table 1 for each example.

This dried powder was calcined for four hours at 500° C. After that, the powder is subjected to the dry sieving process, so that the calcined powder containing the porous silica particles is obtained. The pore size distribution of the porous silica particles is shown in FIG. 1. FIG. 1 indicates that the most frequent pore diameter ($D_m$) of the porous silica particle according to this example is 834 nm, the minimum pore diameter ($D_0$) thereof is 150 nm, and the maximum pore diameter ($D_{100}$) is 1211 nm. FIG. 2 is the SEM photograph (magnification: 10,000) of the external appearance of the porous silica particle. FIG. 3 is the SEM photograph (magnification: 10,000) of the cross section of the porous silica particle. The physical properties of the powder of the porous silica particles are measured by the method to be described below. The results are shown in Table 2.

(1) Method of Measuring Mean Particle Diameter ($d_1$) of Porous Silica Particles The particle size distribution of the porous silica particles was measured by the laser diffraction method. Based on the particle size distribution, the mean particle diameter ($d_1$) represented by the median size was obtained. The measurement of the particle size distribution by the laser diffraction method employed the laser diffraction particle diameter analyzer LA-950 (manufactured by HORIBA, Ltd.).

(2) Method of Measuring Mean Particle Diameter ($d_2$) of Silica Microparticles

The particle size distribution of the silica microparticles was measured using the laser particle analyzer (LP-510, manufactured by Otsuka Electronics Co., Ltd.). Based on the particle size distribution, the mean particle diameter ($d_2$) represented by the median size was obtained.

(3) Method of Measuring Coefficient of Variation of Silica Microparticles

A photograph (SEM photograph) is taken with a magnification of 20,000 to 250,000 using the scanning electron microscope (JSM-7600F, manufactured by JEOL Ltd.). The mean particle diameter of 250 particles in this photograph was measured using the image analyzer (IP-1000, manufactured by Asahi Kasei Corporation). The coefficient of variation (CV value) regarding the particle size distribution was calculated.

(4) Method of Measuring Sphericity of Silica Microparticles

Arbitrary 50 particles were selected from the photograph projection diagram obtained by photographing with a magnification of 20,000 to 250,000 using the transmission electron microscope (H-8000, manufactured by Hitachi, Ltd.). Of each of the selected particles, the maximum diameter (DL) and the short diameter (DS) orthogonal to the maximum diameter (DL) were measured and the ratio (DS/DL) was obtained. The mean value of the ratio was determined as the sphericity.

(5) Method of Measuring Specific Surface Area of Porous Silica Particles

The powder of the porous silica particles was taken by approximately 30 ml in a magnetic crucible (B-2 type), dried for two hours at 105° C., and then cooled down to the room temperature in a desiccator. Next, the sample was taken by 1 g, and the specific surface area ($m^2/g$) thereof was measured based on the BET method using the full-automatic surface area measuring device (Multisorb 12, manufactured by Yuasa Ionics Inc.). The measured specific surface area was converted with a silica gravity of 2.2 $g/cm^3$, so that the specific surface area per unit weight was obtained.

(6) Method of Measuring Pore Volume and Pore Diameter of Porous Silica Particles The powder of the porous silica particles was taken by 10 g into a crucible and dried for one hour at 300° C., and then cooled down to the room temperature in a desiccator. The measurement was conducted by a mercury porosimetry method using the automatic porosimeter (PoreMasterPM33GT, manufactured by Quantachrome Instruments). Mercury was injected while pressure was applied thereto by 1.5 kPa to 231 MPa. The pore size distribution was obtained from the relation between the pressure and the pore diameter. Based on this method, mercury was injected into the pores from approximately 7 nm to approximately 1000 μm. Therefore, both the small-diameter pores existing in the porous silica particles and the large-diameter space (the measurement indicates that the space has a size of 1/5 to 1/2 of the mean particle diameter of the porous silica particles) between the porous silica particles are measured. Based on the results of measuring the small-diameter pores excluding the large-diameter space, the pore volume, the most frequent pore diameter ($D_m$), the minimum pore diameter ($D_0$), and the maximum pore diameter ($D_{100}$) are calculated. Here, the peak separation software (attached to the automatic porosimeter) is used as necessary.

(7) Method of Analyzing Composition of Porous Silica Particles

The powder of the porous silica particles was weighted by 0.2 g on a platinum plate. Then, 10 ml of sulfate and 10 ml of hydrofluoric acid are added thereto and the mixture is heated on the sand bath until the white smoke comes out of sulfate. After the mixture is cooled, approximately 50 ml of water is added and the mixture is dissolved by heat. After the mixture is cooled, the mixture is diluted into approximately 200 ml of water and the resulting mixture is treated as the test solution. With this test solution, the composition of the porous silica particles is obtained using the inductively coupled plasma emission spectrometer (ICPS-8100, Analysis software ICPS-8000, manufactured by Shimadzu Corporation).

(8) Density of Porous Silica Particles

The porous silica particles were taken by approximately 30 ml into a magnetic crucible (B-2 type). The taken particles are dried at 105° C. for two hours, put into a desiccator, and then cooled down to the room temperature. Next, 15 ml of the sample was taken and the true specific gravity thereof was measured using the automatic pycnometer (Ultrapyc1200e, manufactured by Quantachrome Instruments). The obtained measurement value is defined as the particle density.

(9) Mean Number of Contact Points

The porous silica particles for 0.1 g were mixed into 100 g of epoxy resin (Quetol651, manufactured by Nisshin EM Co., Ltd.). This epoxy resin is cured at 60° C. for 24 hours. Next, the cured block is cut with the argon ion beam (cross-section polisher, manufactured by JEOL Ltd., the acceleration voltage is 6.2 kV). With the scanning electron microscope (JSM-7600F, manufactured by JEOL Ltd.), the obtained cross-sectional sample was photographed (SEM photograph) at a magnification of 1,000 to 50,000. From the 10 photographs, the number of contact points between one microparticle in the center of the sphere and the adjacent microparticles is measured. The mean value is rounded to provide the integer, which is defined as the mean contact point number.

Specific description will be made with reference to FIG. 2 and FIG. 3. FIG. 3 is a SEM photograph (magnification: 10,000) of the cross section of the porous silica particle. One porous silica particle according to this example is shown. The microparticle closest to the intersection representing the substantial center of the porous silica particle is the particle marked with a circle at the right side of and below the intersection. It can be understood that the number of contact points between the particle in the center and the adjacent particles (each marked with a triangle) is two.

(10) Compression Strength of Porous Silica Particles

From the powder of the porous silica particles, one of the particles in the range of mean particle diameter ±0.5 μm is taken as a sample. With the micro compression tester (MCTM-200, manufactured by Shimadzu Corporation), the load is applied to this sample at the constant loading speed. The weighting value at which the particle is broken is defined as the compression strength (Mpa). This operation was repeated four times, and the compression strength of five samples was measured. The mean value of the obtained measurement values is defined as the particle compression strength.

(11) Texture Characteristics of Porous Silica Particles

Twenty panelists conduct the sensory test on the powder of the porous silica particles, and the following seven items are examined by hearing from the twenty panelists: the smoothness, the moistness, the rolling effect, the even spreadability, the adhesive property, the continuing rolling effect, and the lowness of the raspy feeling unique to the silica particles. The results are evaluated based on the following criteria (a). Moreover, the points given by the panelists were totaled and the texture of the porous silica particles was evaluated based on the following evaluation criteria (b). The results are shown in Table 3.

(12) How User Feels when Using Powder Foundation

With the powder of the porous silica particles, the powder foundation including the components in the mixing ratio (wt %) shown in Table 4 was formed. That is to say, the powder (component (1)) according to Example 1 and components (2) to (9) were put into a mixer and stirred until they were mixed uniformly. Next, cosmetic components (10) to (12) were added into this mixer and stirred and further mixed uniformly. Next, the resulting cake-like substance was pulverized and then about 12 g was extracted therefrom. The extracted cake-like substance was press-molded in a square metal plate of 46 mm×54 mm×4 mm; thus, the powder foundation was obtained. The twenty panelists conduct the sensory test on the powder foundation. The following six items are examined by hearing from the twenty panelists: (1) the uniform spreading, the moistness, and the smoothness during the application onto the skin; and (2) the uniformity of the cosmetic film, the moistness, and the softness after the application onto the skin. The results are evaluated based on the following criteria (a). Moreover, the points given by the panelists were totaled and how the panelists felt when using the foundation was evaluated based on the following evaluation criteria (b). The results are shown in Table 5.

Evaluation Criteria (a)
  5: Excellent
  4: Good
  3: Average
  2: Poor
  1: Very poor Evaluation Criteria (b)
  Double circular mark: 80 or more points in total
  Single circular mark: 60 or more and less than 80 points in total
  White triangular mark: 40 or more and less than 60 points in total
  Black triangular mark: 20 or more and less than 40 points in total
  Cross mark: less than 20 points in total Example 2

After 153 g of water glass (JIS-3, with a silica concentration of 29 wt %) is added to 2000 g of silica sol (SS-300 with a mean particle diameter of 300 nm and a silica concentration of 20 wt %, manufactured by JGC Catalysts and Chemicals Ltd.), 40 g of cation exchange resin (SK-1B, manufactured by Mitsubishi Chemical Corporation) is added at one time to make the pH 2.5. Then, the cation exchange resin is separated to produce dispersion slurry with a silica sol concentration of 18.6 wt %, a concentration of 2.1 wt % of silicate derived from the water glass, and a total solid content concentration of 20.6 wt %.

The resulting slurry is sprayed and dried under the condition shown in Table 1 in a manner similar to Example 1; thus, the dried powder of the porous silica particles is obtained. This dried powder is calcined at 500° C. for four hours; thus, the powder of the porous silica particles is obtained. The physical properties of this powder were measured by the method similar to that of Example 1. The results are shown in Table 2.

Examples 3 to 12, Comparative Examples 1 to 4

The dried powder was made in a manner similar to Example 1 under the preparation conditions shown in Table 1 instead of the silica sol and the silicate binder used in Example 1. The dried powder is calcined in a manner similar to Example 1; thus, the powder of the porous silica particles is made. The physical properties of the powder according to Example 3 to 12 and the powder according to Comparative Examples 1 to 4 obtained as above were measured by the same method as that of Example 1. The results are shown in Table 2.

Comparative Example 5

The pH of 2000 g of the product (with a silica concentration of 15 wt %) formed by diluting silica sol (SS-160 with a mean particle diameter of 160 nm and a silica concentration of 20 wt %, manufactured by JGC Catalysts and Chemicals Ltd.) with water is adjusted to 2.0 by cation exchange. A silicate solution (with a silica concentration of 4.8 wt %) is added thereto by 694.4 g so that [silica in the silica sol]/[silica in the silicate solution]=9/1; thus, the slurry with a silica sol concentration of 11.1 wt %, a concentration of 1.2 wt % of silicate derived from the silicate solution, and a solid content concentration of 5.0 wt % is prepared. The resulting slurry is used as the spray liquid, and sprayed and dried with a spray drier. Here, into the dry air flow whose entrance temperature is set to 240° C. and exit temperature is set to 50 to 55° C., the slurry was supplied through one of two fluid nozzles with a flow rate of 2 L/hr and gas is supplied through the other nozzle at a pressure of 0.75 MPa. The thusly obtained dried powder was calcined for four hours at 500° C. and was subjected to the dry sieving process, and in this manner, the powder of the porous silica particles was made. The physical properties of the powder were measured in a manner similar to Example 1. The results are shown in Table 2.

TABLE 1

| | | Raw material for spray | Example 1 | Example 2 | Example 3 | Example 4 | Example 5 | Example 6 |
|---|---|---|---|---|---|---|---|---|
| Dispersion slurry | Silica sol (I) | Kind of Silica microparticle | B | A | C | D | B | B |
| | | Mean particle diameter of silica microparticle (d$_2$) (nm) | 550 | 300 | 120 | 1000 | 550 | 550 |
| | | Coefficient of variation of silica microparticle (%) | 8 | 10 | 9 | 6 | 8 | 8 |
| | | Sphericity of silica microparticle | 0.93 | 0.92 | 0.88 | 0.95 | 0.93 | 0.93 |
| | | Silica concentration of dispersion slurry (wt %) | 27.7 | 18.5 | 27.7 | 27.7 | 18.5 | 18.5 |
| | Silicate binder (II) | Kind of silicate binder | Silicate solution | Water glass | Silicate solution | Silicate solution | Silicate solution | Silicate solution |
| | | Silica concentration of dispersion slurry (wt %) | 3.1 | 2.1 | 3.1 | 3.1 | 2.1 | 2.1 |
| | Third component (III) | Kind of third component | — | — | — | — | — | — |
| | | Solid content concentration of dispersion slurry (wt %) | 0.0 | 0.0 | 0.0 | 0.0 | 0.0 | 0.0 |
| Spray liquid | | Weight mixing ratio of raw materials for spray (I/II/III) | 90/10/0 | 90/10/0 | 90/10/0 | 90/10/0 | 90/10/0 | 90/10/0 |
| | | Solid content concentration of spray liquid (wt %) | 30.8 | 20.6 | 30.8 | 30.8 | 20.6 | 20.6 |
| Spraying and drying conditions | | Spraying speed (liter/hour) | 2 | 2 | 2 | 2 | 1 | 3 |
| | | Spraying pressure (MPa) | 0.4 | 0.4 | 0.4 | 0.4 | 0.6 | 0.1 |

| | | Raw material for spray | Example 7 | Example 8 | Example 9 | Example 10 | Example 11 | Example 12 |
|---|---|---|---|---|---|---|---|---|
| Dispersion slurry | Silica sol (I) | Kind of Silica microparticle | E | F | F | F | F | F |
| | | Mean particle diameter of silica microparticle (d$_2$) (nm) | 160 | 160 | 160 | 160 | 160 | 160 |
| | | Coefficient of variation of silica microparticle (%) | 8 | 9 | 9 | 9 | 9 | 9 |
| | | Sphericity of silica microparticle | 0.91 | 0.89 | 0.89 | 0.89 | 0.89 | 0.89 |
| | | Silica concentration of dispersion slurry (wt %) | 27.7 | 19.4 | 19.4 | 19.4 | 19.4 | 19.4 |
| | Silicate binder (II) | Kind of silicate binder | Silicate solution | Silicate solution | Silicate solution | Silicate solution | Silicate solution | Silicate solution |
| | | Silica concentration of dispersion slurry (wt %) | 3.1 | 2.2 | 2.2 | 2.2 | 2.2 | 2.2 |
| | Third component (III) | Kind of third component | — | Styrene-butadiene latex | Titanium dioxide | Diiron trioxide | Iron hydroxide oxide | Triiron tetraoxide |
| | | Solid content concentration of dispersion slurry (wt %) | 0.0 | 9.2 | 9.2 | 9.2 | 9.2 | 9.2 |
| Spray liquid | | Weight mixing ratio of raw materials for spray (I/II/III) | 90/10/0 | 63/7/30 | 63/7/30 | 63/7/30 | 63/7/30 | 63/7/30 |
| | | Solid content concentration of spray liquid (wt %) | 30.8 | 30.8 | 30.8 | 30.8 | 30.8 | 30.8 |
| Spraying and drying conditions | | Spraying speed (liter/hour) | 2 | 2 | 2 | 2 | 2 | 2 |
| | | Spraying pressure (MPa) | 0.4 | 0.4 | 0.4 | 0.4 | 0.4 | 0.4 |

| | | Raw material for spray | Comparative Example 1 | Comparative Example 2 | Comparative Example 3 | Comparative Example 4 | Comparative Example 5 |
|---|---|---|---|---|---|---|---|
| Dispersion slurry | Silica sol (I) | Kind of Silica microparticle | G | H | F | A | F |
| | | Mean particle diameter of silica microparticle (d$_2$) (nm) | 45 | 12 | 160 | 300 | 160 |
| | | Coefficient of variation of silica microparticle (%) | 9 | 12 | 9 | 10 | 9 |
| | | Sphericity of silica microparticle | 0.81 | 0.79 | 0.89 | 0.92 | 0.89 |
| | | Silica concentration of dispersion slurry (wt %) | 27.7 | 27.7 | 4.5 | 4.5 | 11.1 |
| | Silicate binder (II) | Kind of silicate binder | Silicate solution | Silicate solution | Silicate solution | Silicate solution | Silicate solution |
| | | Silica concentration of dispersion slurry (wt %) | 3.1 | 3.1 | 0.5 | 0.5 | 1.2 |
| | Third component (III) | Kind of third component | — | — | — | — | — |
| | | Solid content concentration of dispersion slurry (wt %) | 0.0 | 0.0 | 0.0 | 0.0 | 0.0 |

TABLE 1-continued

| | | | | | | |
|---|---|---|---|---|---|---|
| Spray liquid | Weight mixing ratio of raw materials for spray (I/II/III) | 90/10/0 | 90/10/0 | 90/10/0 | 90/10/0 | 90/10/0 |
| | Solid content concentration of spray liquid (wt %) | 30.8 | 30.8 | 5 | 5 | 12.4 |
| Spraying and drying conditions | Spraying speed (liter/hour) | 2 | 2 | 2 | 2 | 2 |
| | Spraying pressure (MPa) | 0.4 | 0.4 | 0.4 | 0.4 | 0.75 |

Remarks)
Silica microparticle A: manufactured by JGC C&C. SS-300 (mean particle diameter: 300 nm)
Silica microparticle B: manufactured by JGC C&C. SS-550 (mean particle diameter: 550 nm)
Silica microparticle C: manufactured by JGC C&C. SS-120 (mean particle diameter: 120 nm)
Silica microparticle D: manufactured by JGC C&C. SS-1000 (mean particle diameter: 1000 nm)
Silica microparticle E: manufactured by JGC C&C. SP-160 (Silica-alumina microparticle, mean particle diameter: 160 nm)
Silica microparticle F: manufactured by JGC C&C. SS-160 (mean particle diameter: 160 nm)
Silica microparticle G: manufactured by JGC C&C. Cataloid SI-45P (mean particle diameter: 45 nm)
Silica microparticle H: manufactured by JGC C&C. Cataloid SI-30 (mean particle diameter: 12 nm)
Styrene-butadiene latex microparticle: manufactured by JSR Corporation 0602 (mean particle diameter: 180 nm)
Titanium dioxide microparticle: manufactured by ISHIHARA SANGYO KAISHA, LTD. CR-50 (mean particle diameter: 250 nm)
Diiron trioxide microparticle: manufactured by Titan Kogyo, Ltd. R-516P (mean particle diameter: 450 nm)
Iron hydroxide oxide microparticle: manufactured by Titan Kogyo Ltd. LL-100P (mean particle diameter: 450 nm)
Triiron tetraoxide microparticle: manufactured by Titan Kogyo Ltd. BL-100P (mean particle diameter: 200 nm)

TABLE 2

| | | | Example 1 | Example 2 | Example 3 | Example 4 | Example 5 | Example 6 | Example 7 |
|---|---|---|---|---|---|---|---|---|---|
| Porous silica particle | Mean particle diameter ($d_1$) | μm | 5.9 | 5.2 | 5.0 | 10.3 | 2.8 | 20.0 | 5.9 |
| | Specific surface area | m$^2$/cm$^3$ | 12 | 21 | 53 | 7 | 11 | 15 | 24 |
| | Pore volume | ml/g | 0.36 | 0.39 | 0.35 | 0.37 | 0.35 | 0.38 | 0.35 |
| | Most frequent pore diameter ($D_m$) | nm | 834 | 655 | 230 | 1890 | 845 | 671 | 620 |
| | Minimum pore diameter ($D_o$) | nm | 150 | 93 | 55 | 299 | 163 | 201 | 210 |
| | Maximum pore diameter ($D_{100}$) | nm | 1211 | 933 | 519 | 2330 | 890 | 3823 | 1298 |
| | $D_{100}/D_0$ | — | 8 | 10 | 9 | 8 | 5 | 19 | 6 |
| | $d_2/d_1$ | — | 0.09 | 0.06 | 0.02 | 0.10 | 0.20 | 0.03 | 0.03 |
| | Density | g/cm$^3$ | 2.2 | 2.2 | 2.2 | 2.2 | 2.2 | 2.2 | 2.7 |
| | Mean contact point number | — | 2 | 2 | 2 | 2 | 2 | 2 | 2 |
| | Particle compression strength | MPa | 80 | 75 | 85 | 60 | 150 | 50 | 80 |
| | SiO$_2$ | % | 100 | 100 | 100 | 100 | 100 | 100 | 73 |
| | Other component | Kind | — | — | — | — | — | — | Aluminium oxide |
| | | % | — | — | — | — | — | — | 27 |
| | Particle diameter ratio (Silica microparticle/Porous silica particle) | — | 0.09 | 0.06 | 0.02 | 0.10 | 0.20 | 0.03 | 0.03 |

| | | | Example 8 | Example 9 | Example 10 | Example 11 | Example 12 | Comparative Example 1 |
|---|---|---|---|---|---|---|---|---|
| Porous silica particle | Mean particle diameter ($d_1$) | μm | 5.8 | 5.3 | 4.7 | 4.5 | 5.1 | 4.2 |
| | Specific surface area | m$^2$/cm$^3$ | 42 | 31 | 30 | 35 | 29 | 135 |
| | Pore volume | ml/g | 0.98 | 0.39 | 0.35 | 0.35 | 0.37 | 0.36 |
| | Most frequent pore diameter ($D_m$) | nm | 923 | 425 | 436 | 333 | 470 | 89 |
| | Minimum pore diameter ($D_o$) | nm | 253 | 72 | 76 | 70 | 71 | 24 |
| | Maximum pore diameter ($D_{100}$) | nm | 1450 | 763 | 711 | 782 | 711 | 86 |
| | $D_{100}/D_0$ | — | 6 | 11 | 9 | 11 | 10 | 4 |
| | $d_2/d_1$ | — | 0.03 | 0.03 | 0.03 | 0.04 | 0.03 | 0.01 |
| | Density | g/cm$^3$ | 2.2 | 2.8 | 3.1 | 2.8 | 3.1 | 2.2 |
| | Mean contact point number | — | 1 | 2 | 2 | 2 | 2 | 2 |
| | Particle compression strength | MPa | 30 | 110 | 130 | 110 | 120 | 90 |
| | SiO$_2$ | % | 100 | 70 | 70 | 70 | 70 | 100 |
| | Other component | Kind | — | Titanium dioxide | Diiron trioxide | Iron hydroxide oxide | Triiron tetraoxide | — |
| | | % | — | 30 | 30 | 30 | 30 | — |
| | Particle diameter ratio (Silica microparticle/Porous silica particle) | — | 0.03 | 0.03 | 0.03 | 0.04 | 0.03 | 0.01 |

| | | | Comparative Example 2 | Comparative Example 3 | Comparative Example 4 | Comparative Example 5 |
|---|---|---|---|---|---|---|
| Porous silica particle | Mean particle diameter ($d_1$) | μm | 5.5 | 3.0 | 3.4 | 2.0 |
| | Specific surface area | m$^2$/cm$^3$ | 500 | 38 | 23 | 59 |
| | Pore volume | ml/g | 0.35 | 0.18 | 0.17 | 0.23 |
| | Most frequent pore diameter ($D_m$) | nm | 24 | 65 | 126 | 64 |
| | Minimum pore diameter ($D_o$) | nm | 13 | 49 | 103 | 54 |
| | Maximum pore diameter ($D_{100}$) | nm | 65 | 70 | 140 | 73 |
| | $D_{100}/D_0$ | — | 5 | 1 | 1 | 1 |
| | $d_2/d_1$ | — | 0.00 | 0.05 | 0.09 | 0.08 |

TABLE 2-continued

| | | | | | |
|---|---|---|---|---|---|
| Density | g/cm³ | 2.2 | 2.2 | 2.2 | 2.2 |
| Mean contact point number | — | 2 | 6 | 6 | 5 |
| Particle compression strength | MPa | 80 | 460 | 400 | 310 |
| SiO₂ | % | 100 | 100 | 100 | 100 |
| Other component | Kind | — | — | — | — |
| | % | — | — | — | — |
| Particle diameter ratio (Silica microparticle/Porous silica particle) | — | 0.00 | 0.05 | 0.09 | 0.08 |

[Texture Characteristics of Powder of Porous Silica Particles]

The texture characteristics of the powder according to Examples and Comparative Examples were evaluated by the same method as that of Example 1. The results are shown in Table 3. The results indicate that the powder according to Examples was excellent as the texture improver for the cosmetic but the powder according to Comparative Examples was not suitable as the texture improver.

TABLE 3

| Evaluation sample | Smoothness | Moistness | Rolling effect | Even spreadability | Adhesive property | Continuing rolling effect | Less raspy feeling |
|---|---|---|---|---|---|---|---|
| Example 1 | ○ | ◎ | ○ | ◎ | ◎ | ◎ | ◎ |
| Example 2 | ○ | ○ | ○ | ○ | ◎ | ○ | ○ |
| Example 3 | ○ | ○ | ○ | ◎ | ◎ | ○ | ○ |
| Example 4 | ○ | △ | ○ | ○ | ◎ | ○ | △ |
| Example 5 | △ | ◎ | ○ | ○ | ◎ | △ | ◎ |
| Example 6 | ◎ | △ | ◎ | ◎ | ○ | ◎ | ◎ |
| Example 7 | ○ | ○ | ○ | ○ | ◎ | ◎ | ○ |
| Example 8 | ○ | ○ | △ | △ | ◎ | △ | ○ |
| Example 9 | ○ | ○ | ○ | ◎ | ○ | ○ | ○ |
| Example 10 | ○ | ○ | ○ | ◎ | ○ | ○ | ○ |
| Example 11 | ○ | ○ | ○ | ◎ | ○ | ○ | ○ |
| Example 12 | ○ | ○ | △ | ◎ | ○ | ○ | ○ |
| Comparative Example 1 | ◎ | X | ◎ | △ | △ | ◎ | X |
| Comparative Example 2 | ◎ | X | ◎ | △ | △ | ◎ | ▲ |
| Comparative Example 3 | ○ | △ | ○ | ○ | ▲ | ○ | △ |
| Comparative Example 4 | ○ | △ | ○ | ○ | △ | ○ | ○ |
| Comparative Example 5 | △ | ○ | △ | △ | ○ | △ | △ |

[How User Feels when Using Powder Foundation]

The powder (the component (1)) according to Examples and Comparative Examples and the components (2) to (9) were put into a mixer according to the mixing ratio (wt %) shown in Table 4 and stirred until they were mixed uniformly. Next, the cosmetic components (10) to (12) were put into this mixer and stirred and further mixed uniformly. With the resulting cake-like substance, the cosmetic similar to that of Example 1 was obtained.

TABLE 4

| Cosmetic components of powder foundation | Mixing amount/wt % |
|---|---|
| (1) Powder according to Examples 1 to 3 and Comparative Examples 1 to 3 | 10.0 |
| (2) Sericite (silicone surface treatment) | 40.0 |
| (3) Talc (silicone surface treatment) | 29.0 |
| (4) Mica (silicone surface treatment) | 5.0 |
| (5) Titanium oxide (silicone surface treatment) | 7.0 |
| (6) Yellow iron oxide (silicone surface treatment) | 1.2 |
| (7) Red oxide (silicone surface treatment) | 0.4 |
| (8) Black iron oxide (silicone surface treatment) | 0.2 |
| (9) Methylparaben | 0.2 |
| (10) Dimethicone | 4.0 |
| (11) Liquid paraffin | 2.0 |
| (12) Glyceryl tri-2-ethylhexanoate | 1.0 |

Next, how the user felt when using the cosmetic obtained as above (the texture during the application and the texture after the application) was examined by the same method as that of Example 1. The results are shown in Table 5. It has been understood that the cosmetics A to C according to Examples are excellent either during or after the application but the cosmetics a to c according to Comparative Examples are not very good.

TABLE 5

|  | In application | | | After application | | |
|---|---|---|---|---|---|---|
| Evaluation sample | Even spreadability | Moistness | Silkiness | Uniformity of application coat | Moistness | Softness |
| Example 1 (Cosmetic A) | ◎ | ◎ | ◎ | ◎ | ◎ | ◎ |
| Example 2 (Cosmetic B) | ○ | ○ | ○ | ○ | ○ | ○ |
| Example 3 (Cosmetic C) | ○ | ○ | ◎ | ◎ | ○ | ○ |
| Comparative Example 1 (Cosmetic a) | ◎ | X | X | △ | △ | X |
| Comparative Example 2 (Cosmetic b) | ◎ | X | ▲ | △ | △ | X |
| Comparative Example 3 (Cosmetic c) | ○ | △ | △ | ○ | ▲ | △ |

The invention claimed is:

1. A porous silica particle comprising:
   silica microparticles comprising:
   a mean micro-particle diameter ($d_2$) of more than 100 nm and 1000 nm or less,
   a sphericity of 0.85 to 1, and
   a CV-value of less than 15%,
   wherein the porous silica particle comprises:
   a mean particle diameter ($d_1$) of 0.5 to 25 µm,
   a specific surface area obtained by the BET method of 5 to 60 m$^2$/cm$^3$, and
   a pore volume of 0.35 to 2.0 ml/g,
   wherein in a pore size distribution (X axis: pore diameter, Y axis: value obtained by differentiating pore volume by pore diameter) of the porous silica particle, the minimum pore diameter ($D_0$) is in the range of 25 to 500 nm, the maximum pore diameter ($D_{100}$) is in the range of 300 to 8000 nm, and the ratio of the maximum pore diameter ($D_{100}$) to the minimum pore diameter ($D_0$), ($D_{100}/D_0$), is in the range of 4 to 320.

2. The porous silica particle according to claim 1, wherein in the pore size distribution (X axis: pore diameter, Y axis: value obtained by differentiating pore volume by pore diameter) of the porous silica particle, the most frequent pore diameter ($D_m$) satisfies 100 <$D_m$<4000 [nm].

3. The porous silica particle according to claim 1, further comprising inorganic oxide microparticles in the range of 10 to 50 wt %, the inorganic oxide microparticles containing at least one of titanium dioxide, iron oxide, and zinc oxide.

4. The porous silica particle according to claim 1, wherein the silica microparticles mean micro-particle diameter ($d_2$) comprises the range of 0.01 to 0.30 times the mean particle diameter ($d_1$) of the porous silica particle.

5. A cosmetic comprising the porous silica particle according to claim 1.

6. The porous silica particle according to claim 1,
   wherein individual silica microparticles comprise a specific surface area obtained by the BET method of 5 to 60 m$^2$/cm$^3$ and a pore volume of 0.35 to 2.0 ml/g; and
   wherein the porous silica particle comprises a plurality of sparsely packed individual silica microparticles.

7. The porous silica particle according to claim 1, wherein the porous silica particle is used in cosmetics.

8. A porous silica particle comprising silica microparticles, the porous silica particle comprising a mean particle diameter ($d_1$) of 0.5 to 25 µm, a specific surface area obtained by the BET method of 5 to 60 m$^2$/cm$^3$, and a pore volume of 0.35 to 2.0 ml/g wherein in a pore size distribution (X axis: pore diameter, Y axis: value obtained by differentiating pore volume by pore diameter) of the porous silica particle, the minimum pore diameter ($D_0$) is in the range of 25 to 500 nm, the maximum pore diameter ($D_{100}$) is in the range of 300 to 8000 nm, the ratio of the maximum pore diameter ($D_{100}$) to the minimum pore diameter ($D_0$), ($D_{100}/D_0$), is in the range of 4 to 320, and a most frequent pore diameter ($D_m$) satisfies 100<$D_m$<4000 nm.

* * * * *